(12) United States Patent
Courage et al.

(10) Patent No.: US 7,115,671 B2
(45) Date of Patent: Oct. 3, 2006

(54) PROCESS FOR RECOVERING MONOMERIC UNITS OF A NYLON FROM WHOLE CARPET

(75) Inventors: Antonius J. F. M. Courage, Stein (NL); Marco J. A. Houben, Sittard (NL); Mathieu H. M. Mertens, Sittard (NL); Leonardus J. G. Raets, Elsloo (NL)

(73) Assignee: DSM IP Assets B.V., Heerlen (NL)

( * ) Notice: Subject to any disclaimer, the term of this patent is extended or adjusted under 35 U.S.C. 154(b) by 137 days.

(21) Appl. No.: 10/159,982

(22) Filed: Jun. 3, 2002

(65) Prior Publication Data

US 2003/0225170 A1    Dec. 4, 2003

Related U.S. Application Data

(63) Continuation of application No. PCT/NL00/00884, filed on Dec. 1, 2000.

(30) Foreign Application Priority Data

Dec. 3, 1999    (EP)    ................................... 99204107

(51) Int. Cl.
  *C08J 11/04*    (2006.01)
(52) U.S. Cl. ...................... 521/49.8; 521/40; 521/40.5; 241/14; 241/24.12; 241/24.18; 241/24.19; 241/24.21; 83/27
(58) Field of Classification Search ................. 521/40, 521/40.5, 49.8; 241/14, 24.12, 24.18, 24.19, 241/24.21; 83/27
See application file for complete search history.

(56) References Cited

U.S. PATENT DOCUMENTS 5,062,949 A    11/1991  Hausmann
5,169,870 A  * 12/1992  Corbin et al. ............... 521/49.8
5,304,576 A  *  4/1994  Martinez ...................... 521/41
5,457,197 A  * 10/1995  Sifniades et al. ........... 540/540
5,518,188 A     5/1996  Sharer
5,535,945 A  *  7/1996  Sferrazza et al. ........ 241/24.12
5,990,306 A  * 11/1999  Mayer et al. ............... 540/540
6,111,099 A  *  8/2000  Frentzen et al. ............ 540/540

FOREIGN PATENT DOCUMENTS

| | | |
|---|---|---|
| EP | 522 235 | 1/1993 |
| EP | 728 565 | 8/1996 |
| WO | 94 06763 | 3/1994 |
| WO | 97 29713 | 6/1997 |

OTHER PUBLICATIONS

"PA 6-Recycling zu Caprolactam aus textilen Bodenbelagen", Chemiefasert/Textilindustrie, DE, Deutscher Fachverlag GMBH. Frankfurt AM, Main., vol. 42, No. 6, Jun. 1992, p. 497.

* cited by examiner

*Primary Examiner*—Vasu Jagannathan
*Assistant Examiner*—Vickey Ronesi
(74) *Attorney, Agent, or Firm*—Mayer, Brown, Rowe & Maw LLP

(57) ABSTRACT

The invention relates to a process for recovering monomeric units of a nylon from carpet material. The carpet material includes fibres containing nylon bound to a backing containing one or more non-nylon components. The carpet material contains between 15 and 35 wt. % of the nylon. The process includes:
a) mechanically separating the carpet material into an enriched carpet mixture containing between 35 and 55 wt. % of said nylon and into a depleted carpet mixture having a lower content of nylon than the carpet material; and
b) exposing the enriched carpet mixture to conditions at which depolymerization of the nylon is effected.

23 Claims, 3 Drawing Sheets

PROCESS FOR RECOVERING MONOMERIC UNITS OF A NYLON FROM WHOLE CARPET

This application is a continuation of International PCT/NL00/00884 filed on Dec. 1, 2000.

BACKGROUND OF THE INVENTION

The invention relates to a process for recovering monomeric units of a nylon from carpet material.

It is known that monomeric units of a nylon can be recovered from carpet material, in particular from waste carpet material.

WO-A-9720813 describes a depolymerisation process in which caprolactam is recovered from nylon-6 containing carpets. It is described that carpets are size reduced by mechanical treatment, after which depolymerization of the nylon is effected.

U.S. Pat. No. 5,169,870 discloses a process for the recovery of caprolactam from nylon-6 carpet in which a large portion of the backing is removed from the carpet in a mechanical separator before it is fed to a depolymerization reactor.

EP-A-728565 describes a process for reclaiming polymeric fibres from carpeting using a series of mechanical steps. It is described that a carpet mixture can be obtained which preferably contains between about 75 to about 85 wt. %. of nylon particulates. It is described that the product obtained is in particular suitable for the process described in U.S. Pat. No. 5,169,870. In the process of EP-A-728565 many mechanical steps are used. This is disadvantageous in view of operating and investment costs.

The references cited above disclose processes in which the carpets used as a starting material have a nylon content of about 50 wt. % or higher. However, a significant fraction of the carpets available for recycling, in particular carpets for the European market, contain between 15 to 35 wt. % nylon.

It is an object of the invention to provide an efficient process for recovering monomeric units of a nylon from carpet carpet material which contains between 15 to 35 wt. % nylon.

BRIEF SUMMARY OF THE INVENTION

This object is achieved by providing a process for recovering monomeric units of a nylon from carpet material, said carpet material comprising fibres containing said nylon bound to a backing containing one or more non-nylon components, the carpet material containing between 15 and 35 wt. % of said nylon, which process comprises the steps of:

a) mechanically separating the carpet material into an enriched carpet mixture containing between 35 and 55 wt. % of said nylon and into a depleted carpet mixture having a lower content of said nylon than the carpet material b) exposing the enriched carpet mixture to conditions at which depolymerisation of said nylon is effected.

According to the invention a good yield of monomeric units can be obtained using a small number of steps. Furthermore, transport of molten carpet streams prior to, during and/or after depolymerisation is facilitated.

The invention also relates to a process for recovering a carpet mixture from carpet material, said carpet material comprising fibres containing said nylon bound to a backing containing one or more non-nylon components, the carpet material containing between 15 and 35 wt. % of said nylon, which process comprises the step of:

a) mechanically separating the carpet material into an enriched carpet mixture containing between 35 and 55 wt. % of said nylon and into a depleted carpet mixture having a lower content of said nylon than the carpet material.

According to this aspect of the invention, a good yield of nylon can be obtained using a small number of process steps. The resulting enriched carpet mixture can efficiently be used in a depolymerisation process, and can efficiently be transported in the molten state.

Obtaining an enriched carpet mixture in step a) containing less than 55 wt. % of said nylon has the advantage that good yields of monomeric units and/or nylon can be obtained using a small number of process steps. Further decreasing the content of said nylon in the enriched carpet mixture has the advantage that the yield of nylon and/or monomeric units is higher for a given number of process steps and/or that the number of process steps can be decreased to obtain a given yield of monomeric units and/or nylon. Preferably, an enriched carpet mixture is obtained in step a) containing less than 52 wt. %, more preferably less than 50 wt. %, in particular less than 48 wt. % of said nylon.

Obtaining an enriched carpet mixture in step a) containing more than 35 wt. % of said nylon has the advantage that the processability is improved due to a decreased viscosity at temperatures at which depolymerisation is effected. Preferably, an enriched carpet mixture is obtained in step a) containing more than 38 wt. %, preferably more than 40 wt. % of said nylon.

Preferably, the enriched carpet mixture contains between 38 and 52 wt. % of said nylon, more preferably, between 38 and 50 wt. % of said nylon, in particular between 40 and 48 wt. % of said nylon.

As used herein, the weight percentages of said nylon, also referred to as nylon content, in a material or mixture are given with respect to the total weight of the material or mixture, thus with respect to the sum weight of the nylon and non-nylon materials. The yield of the monomeric units is understood to be the number of monomeric units which are recovered from a given amount of carpet material divided by the number of monomeric units originally present (in polymerised form) in said amount of carpet material. The yield of nylon is understood to be the weight of nylon in the enriched carpet mixture divided by the weight of nylon in the carpet material prior to the mechanical separation of step a.

The carpet material contains between 15 and 35 wt. %, preferably between 18 and 32, more preferably between 20 and 30 wt. % of said nylon. As a carpet material whole carpet and/or strips of whole carpet may advantageously be used. As used herein whole carpet denotes material of which the fibres are still bound to the backing, the backing being essentially intact. "Fibre" denotes an elongated body, the length dimension of which is much greater than the transverse dimensions of width and thickness. The fibers contain a nylon. Typically, the fibres contain predominantly a nylon. A nylon may, for instance, be nylon-6, nylon-6,6, or nylon-4,6. Monomeric components for nylon-6 include caprolactam. Monomeric components for nylon-6,6 include hexamethylene diamine and adipic acid. The backing contains one or more non-nylon components, such as for instance polypropylene, calcium carbonate, styrene butadiene rubber, or jute. Typically, the backing contains predominantly one or more non-nylon components.

Step a) is not limited to specific mechanical separation steps. Mechanical steps which are known in the art, such as for instance shredding, tearing, hammering, screening, granulation and air classification steps or combinations there of may be used.

Preferably, step a) comprises the steps of:

a1) mechanically treating the carpet material (1), so as to size reduce the backing and to loosen at least part of the fibres from the backing, resulting in a primary loosened carpet mixture (2) comprising backing particles and fibres a2) sieving the primary loosened carpet mixture (2) to obtain a primary rich carpet mixture (3) and a primary poor carpet mixture (4), the primary rich carpet mixture having a higher content of said nylon than the primary loosened carpet mixture, the primary poor carpet mixture having a lower content of said nylon than the primary loosened carpet mixture.

Preferably, the primary loosened carpet mixture contains loosened fibres. A loosened fibre is understood to be a fibre which is not bound to a portion of the backing or a fibre which is bound to a portion of the backing, the total weight of said portion being less than the weight of said fibre. Said loosened fibres may form clusters in which other particles, for instance backing particles may be entangled. It will be understood that such entangled backing particles are not considered to be bound to the loosened fibres. Preferably, at least 15 wt. %, more preferably at least 20 wt. %, in particular at least 25 wt. %, more in particular at least 30 wt. % of the fibres in the primary loosened carpet mixture are loosened fibres. Said percentages are given with respect to the total weight of fibres in the primary loosened carpet mixture. Preferably, the primary loosened carpet mixture comprises backing particles having a diameter lower than 30 mm, more preferably lower than 20 mm, in particular lower than 10 mm. Preferably, step a1 is carried out so as to pulverize and loosen the backing from the fibres while leaving the fibres essentially intact.

Step a1) may for instance be effected by shredding, tearing, hammering, granulation and/or combinations thereof. Step a1) may be carried out by shredding whole carpet into strips and impacting said strips against an aperture anvil plate with hammer elements. A process in which carpeting is shredded into strips and in which the strips are impacted against an aperture anvil plate is for instance described in EP-A-728565, the contents of which are herewith incorporated by reference. Said impacting may for instance be effected using a hammer mill. Conventional shredders and hammer mills may be used. Preferably, step a1) is carried out using a shredder with knives, the knives being sufficiently blunt to effect loosening of at least part of the fibres from the backing and size reduction of the backing. Preferably, the knives of the shredder are sufficiently blunt to loosen at least 15 wt. % of the fibres from the backing, more preferably at least 20 wt. %, in particular at least 25 wt. %, more in particular at least 30 wt. %. This embodiment has the advantage that in one single step a loosened mixture of backing particles and fibres can be obtained from whole carpet, which whole carpet has not been subjected to any prior mechanical separation step. However, strips of whole carpet may me fed to said shredder too. It is noted that in case of the usual operation of a shredder, which has for instance been described in EP-A-728565, the knives are sufficiently sharp to cut the whole carpet into strips. In that case the fibres are not loosened from the backing, so that an additional hammering step is used. If the knives of the shredder are sufficiently blunt, one single mechanical separation step is sufficient to obtain a loosened carpet mixture from whole carpet even if this has not been cut into strips.

Therefore, the invention also relates to a process for obtaining a carpet mixture comprising fibres and backing particles from whole carpet and/or strips of whole carpet, said whole carpet comprising said fibres bound to a backing, which process involves feeding the whole carpet and/or strips of whole carpet to a shredder, said shredder being provided with knives which are sufficiently blunt to effect size reduction of the backing and loosening of at least part of the fibres from the backing. Preferably, at least 15 wt. % of the fibres from the backing, more preferably at least 20 wt. %, in particular at least 25 wt. %, more in particular at least 30 wt. % is loosened from the backing, i.e. preferably at least 15 wt. %, more preferably at least 20 wt. %, in particular at least 25 wt. % more in particular at least 30 wt. % of the fibres in the loosened carpet mixture obtained from the shredder are loosened fibres. This process is in particular advantageous for whole carpet which has not been subjected to any mechanical separation step. A preferred embodiment of this process is described with reference to FIG. 3. The shredder preferably comprises a rotor (101) with knives (102) attached to it, the rotor being mounted in a housing (103). Carpet material (104), preferably whole carpet, may be fed to an opening (105) in said housing. The rotor is preferably at least partly surrounded by a screen (106) which is preferably parallel to the axis of the rotor. The screen may form part of the housing. Preferably, one or more counter knives (107) are attached to the housing and/or to the screen such that materials can subjected to the joint action of the knives attached to the rotor and the one or more counter knives attached to the housing and/or screen. The carpet material is preferably pushed against the rotor using a pushing device (108). Preferably, a shredder is used which is provided with one single rotor in the housing. This has the advantage that entanglement of whole carpet between the rotors is avoided. Preferably the diameter of the openings in the screen is between 5 and 60 mm, more preferably between 10 and 40 mm. An increasing diameter of the openings has generally the effect that the backing is size reduced to a lesser extent. A decreasing diameter of the openings has generally the effect that the amount of carpet which may be treated per unit of time, is decreased. Preferably, the rotation speed of the rotor is less than 300 revolution per minute (rpm), more preferably less than 200 rpm. Preferably, the rotation speed of the rotor is higher than 50 rpm, more preferably higher than 100 rpm.

The invention is not limited to a specific type of shredding apparatus. A very suitable shredder is the VAZ 300/250 UNF shredder which is manufactured by Vecoplan Maschinefabrik GMBH. As blunt knives may for instance be used knives which have not been sharpened.

Screens known in the art may be used for carrying out step a2), for instance shaking screens, rotating drum screens, optionally in combination with gas flushing. Preferably, step a2) is carried out using an elastic, deformable screen. This has the advantage that blocking of the openings of the screen by fibres or backing particles is minimized. An elastic, deformable screen may be made of an elastic material, for instance rubber. Energy may be supplied to said screen during the sieving, for instance by stretching and bending the screen, usually in an alternating way. An example of an elastic, deformable screen is described in U.S. Pat. No. 5,062,949. Various sizes for the openings of the screen may be used. Preferably, the radius of the circumscribed circle of the openings is between 1 and 100 mm, more preferably between 2 and 50 mm.

The primary rich carpet mixture has a higher nylon content than the primary loosened carpet mixture fed to the screen. Preferably, an overs fraction, i.e. a fraction comprising backing particles and/or fibres which are recovered from a screen without having been transported through the openings of the screen, is included in the primary rich carpet mixture. Typically, an overs fraction has a higher nylon content, than the unders fraction, i.e. a fraction comprising backing particles and/or fibres which have been transported through the openings of the screen. It is possible that an unders fraction is sieved again, for instance by using a second screen having openings which sizes are different from those in the first screen. The overs fraction of this second screening operation may then be combined with the overs fraction of the first screening operation to form the primary rich carpet mixture.

Preferably, sieving step a2) is carried out in such a way that the nylon content of the primary rich carpet mixture is between 35 and 55 wt. %. This has the advantage that a good sieving yield, is obtained. The primary rich carpet mixture may then advantageously be included in the enriched carpet mixture without further separation steps for increasing its nylon content. We have found that the sieving yield is further improved when the upper limit for the content of the nylon in the primary rich carpet mixture is further decreased. The sieving yield is understood to be the total mass of the desired nylon in the primary rich carpet mixture divided by the total mass of said nylon in the primary loosened carpet mixture prior to screening. Preferably, the nylon content of the primary rich carpet mixture is between 38 and 52 wt. %, in particular between 38 and 50 wt. %, more in particular between 40 and 48 wt. %. The nylon content of the primary rich carpet mixture may be controlled in various ways, for instance by varying the residence time and/or the size of the openings in the screen. If the carpet mixture is sieved into more than two fractions, the nylon content of the primary rich carpet mixture may be varied by making various combinations of fractions.

Preferably, step a) further comprises the steps of:

a3) mechanically separating the primary poor carpet mixture into a secondary rich carpet mixture and a secondary poor carpet mixture, the secondary rich carpet mixture having a higher content of said nylon than the primary poor carpet mixture, the secondary poor carpet mixture having a lower content of said nylon than the primary poor carpet mixture.

The secondary rich carpet mixture may advantageously be included in the enriched carpet mixture. Step a3) may be carried out using any known technique, for instance by shredding, hammering, screening, granulation, air classification, or combinations thereof.

Preferably, step a3 comprises the steps of:

i) mechanically treating the primary poor carpet mixture so as to loosen fibres in the primary poor carpet mixture from backing particles in the primary poor carpet mixture, resulting in a secondary loosened carpet mixture.

ii) Sieving the secondary loosened carpet mixture to obtain a secondary rich carpet mixture and a secondary poor carpet mixture, the secondary rich carpet mixture having a higher content of said nylon than the secondary loosened carpet mixture, the secondary poor carpet mixture having a lower content of said nylon than the secondary loosened carpet mixture.

Step i) may for instance be carried out using a hammer mill, an impact mill, an attrition mill or and/or a granulator. Step ii) may for instance be carried out using a vibrating screen, and/or rotating drum screen. Preferably, the radius of the circumscribed circle of the openings in the screen is between 50 and 2000 micrometer, more preferably between 200 and 1000 micrometer.

Preferably, after step i) and prior to step ii) the secondary loosened carpet mixture is subjected to an air classification step in which backing particles are separated from the secondary loosened carpet mixture. The air separation step may for instance be carried out using a wind sifter.

Preferably, the backing particles which are separated in the air classification step include styrene butadiene rubber (SBR) particles. We have found that separation of SBR containing particles facilitates further sieving.

The process according to the invention is not limited to recovering of monomeric units of a specific nylon. The process is in particular suitable if, the nylon is nylon-6.

Step b) is not limited to specific method.

Usually, the depolymerisation is conducted at a temperature of more than 250° C., preferably more than 280° C., more preferably more than 300° C. Typically, the depolymerisation is conducted at a temperature of below 400° C., preferably below 350° C., more preferably below 340° C. In a preferred embodiment the depolymerisation is carried out in the range of 280–340° C. The depolymerisation may be carried out at reduced, atmospheric or increased pressure. Preferably, the depolymerisation is carried out in the presence of a depolymerizing agent, such as for instance water, steam, alcohol, ammonia, or amines. Most preferably, the depolymerisation is carried out in the presence of water or steam. The depolymerisation may be effected in the presence or in the absence of a catalyst.

Preferably, the depolymerisation is effected in the absence of a catalyst. Any type of reactor in which nylon may be depolymerised may be used, such as for instance a continuous stirred tank reactor, a tubular reactor or a series of reactors. If the process according to the invention is used for recovering caprolactam from whole carpet comprised of nylon-6, the depolymerisation may for instance be effected using the methods taught by WO-A-9618613 or U.S. Pat. No. 5,169,870. If the process according to the invention is used for recovering caprolactam from carpet material containing nylon-6, step b preferably comprises the step b1) contacting the beneficiated carpet mixture with superheated steam at a temperature of about 250° C. to about 400° C. and at a pressure within the range of about 1 atm. to about 100 atm. and substantially less than the saturated vapor pressure of water at said temperature wherein a caprolactam-containing vapor stream is formed. This method has been described in U.S. Pat. No. 5,681,952, the content of which is herewith incorporated by reference.

DETAILED DESCRIPTION OF THE INVENTION

Figure 1:
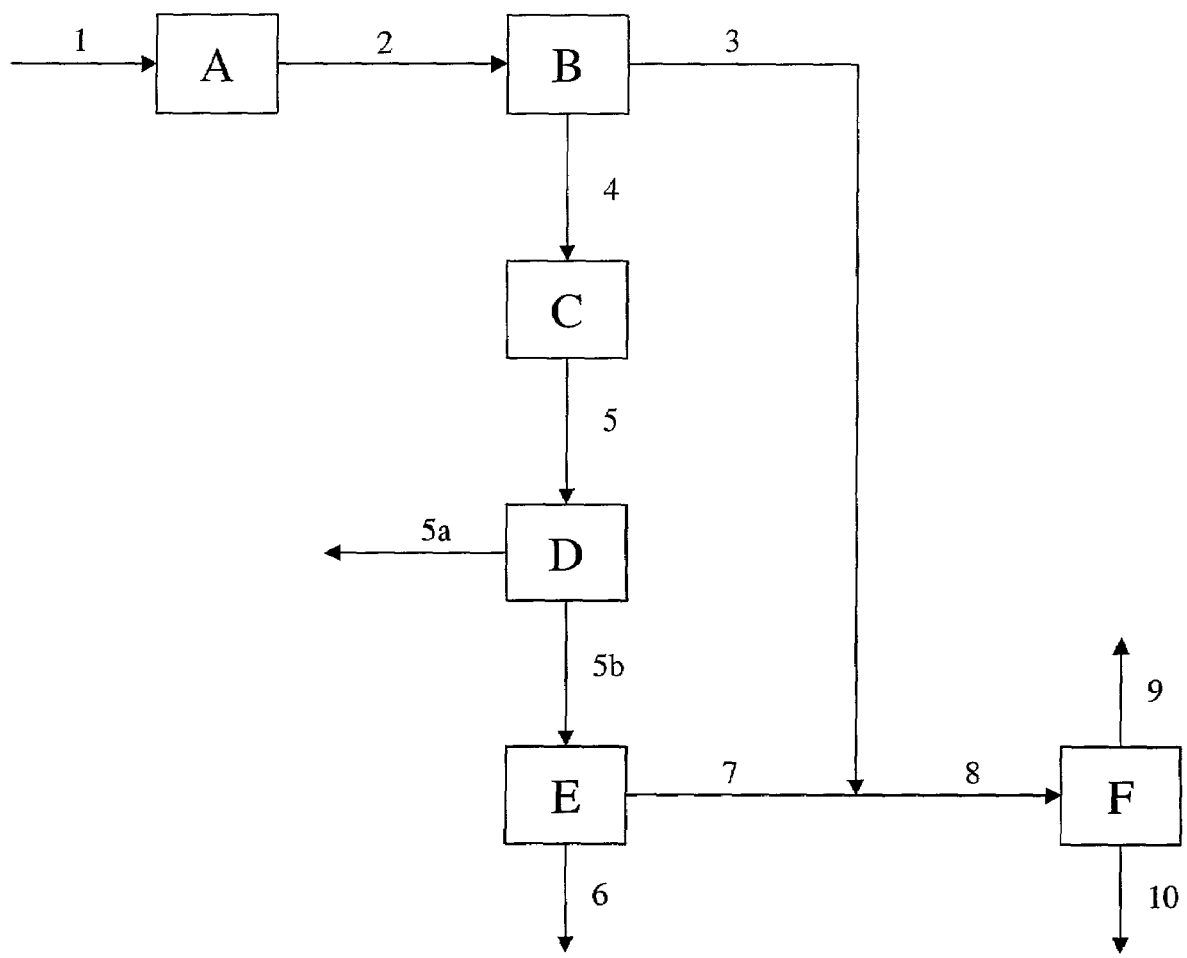
FIG. 1 shows a flow chart of a preferred embodiment of the process according to the invention.

A preferred embodiment of the process according to the invention will be described below with reference to FIG. 1.

1000 kg of Carpet material (1) having a nylon-6 content of 25 wt. % is fed to mechanical size reduction apparatus A. The carpet material is whole carpet which has not been subjected to any mechanical separation step. Mechanical size apparatus A is a shredder (for instance a Vecoplan VAZ 250/300 shredder) to which blunt knives are attached. In said shredder loosening of fibres from the backing is effected. A primary loosened carpet mixture (2) is withdrawn from the shredder and fed to sieving apparatus B. Sieving apparatus B is includes elastic, deformable screens (for instance a bivi-TEC double decks screening machine, designed by Binder & Co. AG, Germany). Primary rich carpet mixture (3) (overs fraction) (250 kg, nylon content 40 wt. %) and primary poor carpet mixture (4) (unders fraction) (750 kg, nylon content 20 wt. %) are withdrawn from sieving apparatus B. Primary poor carpet mixture (4) is fed to mechanical impacting apparatus C. Mechanical impacting apparatus C is a hammer mill (for instance an Oniplex Ha 100/100, manufactured by Alpine Aktiengesellschaft, Augsburg, Germany). In mechanical impacting apparatus C further loosening of fibres from the backing particles is effected. Secondary loosened carpet mixture (5) is withdrawn from mechanical impacting apparatus C and fed to air classification apparatus D. Air classifacation apparatus D is a wind sifter (for instance, a Multi-Plex Zigzag classifier Model MZM, manufactured by Alpine AG, Germany). In air classification apparatus D backing particles (in particular styrene butadiene rubber) and some nylon is withdrawn via stream (5a) (via the bottom of the wind sifter), and secondary loosened carpet mixture (5b) is recovered (560 kg, 23 wt. % nylon). Secondary loosened carpet mixture (5b) is fed to sieving apparatus E. Sieving apparatus E is a vibrating screen (for instance a Rotex Type 112, manufactured by Thomas Locker SA, Wavre-Limal, Belgium). Secondary rich carpet mixture (7) (overs fraction) (280 kg, nylon content 40 wt. %) and secondary poor carpet mixture (6) (unders fraction) (280 kg, nylon content 7 wt. %) are withdrawn from sieving apparatus E. Primary rich carpet mixture (3) and secondary rich carpet mixture (7) are combined to form enriched carpet mixture (8) (530 kg, nylon content 40 wt. %). The nylon yield is 85%. Enriched carpet mixture (8) is fed to depolymerisation apparatus F.

In depolymerisation apparatus F, the 530 kg enriched carpet mixture (8) is molten at a temperature of 300° C., and continuously fed to a first reactor (flow rate about 65 kg/hour). Superheated steam of 400° C. is continuously blown through the bottom of the reactor, the flow rate of the steam being about 85 kg/hour. The pressure in the first reactor is about 1 MPa. A first caprolactam-containing vapour product stream (9) is recovered from the top of the first reactor (for instance a horizontal reactor having a volume of 160 l). A first molten, nylon-6 depleted residue is continuously withdrawn from the bottom of the first reactor, and fed to a second reactor (for instance a horizontal reactor having a volume of 160 l). Superheated steam of 370° C. is continuously blown through the bottom of the second reactor, the flow rate of the steam being about 60 kg/hour. The pressure in the second reactor is about 1 MPa. A second caprolactam-containing vapour product stream (9) is continuously recovered from the top of the second reactor. A second molten, nylon 6 depleted residue (10) is continuously withdrawn from the bottom of the second reactor (flow rate about 43 kg/hour). No catalysts are present during the process. On completion of the process, 163 kg of caprolactam is obtained. This corresponds to a yield of caprolactam of 65% (with respect to the nylon-6 present in the 1000 kg of carpet material). No problems with transport of molten carpet streams occur.

Further preferred embodiments of the invention will now be be elucidated with reference to the following examples, without however being limited thereto.

EXAMPLES

- a VAZ 300/250 UNF shredder which is manufactured by Vecoplan Maschinefabrik GMBH was used which was provided with a screen of which the openings had a diameter of 30 mm and with a rotor to which 56 blunt knives and no sharp knives were attached.
- a bivi-TEC double decks screening machine, designed by Binder & Co. AG, Germany, and manufactured by Jöst, Munster, Germany were used. The screening machine contained two sieve decks, one sieve deck mounted below the other. The decks could each be provided with 14 elastic, deformable sieve plates with a width of 0.4 metre and a length of 1.5 m. Each of these sieve plates could have one of the following opening sizes: 2×8 mm, 3×10 mm, 10×24 mm, 15×25 mm, 22×30 mm, 26×32 mm or 28×35 mm.

Example I

Carpets which had not been shredded into strips (average composition 27.3 wt. % nylon-6, 4.6 wt. % polypropylene, 39.0 wt. % $CaCO_3$ and 27.9 wt. % styrene butadiene rubber) were fed to the shredder at an average rate of 2500 kg/hour. The shredder was operated at 150 rpm. A loosened carpet mixture comprised of backing particles and nylon fibres was recovered from the shredder. The loosened carpet mixture was fed to the upper deck of the screening machine. The upper deck was provided with 7 sieve plates with openings of 26×32 mm and 7 sieve plates with openings of 28×35 mm, placed in random order. The lower deck was provided with 7 sieve plates with openings of 2×8 mm and 7 sieve plates with openings of 3×10 mm, placed in random order. Three streams of material were obtained which were continuously recovered. At some point in time 480 kg material with a nylon content of 47.1 wt. % had been recovered, which had not been transported through the openings of the upper deck (overs fraction from upper deck), 2710 kg material with a nylon content of 33.7 wt. %, which had been transported through the openings of the upper deck, but not through the openings of the lower deck (overs fraction from lower deck), and 1330 kg material with a nylon content of 10.7 wt. % which had passed through the openings of both decks (unders fraction from lower deck).

The overs fraction from the upper deck can be used as a primary rich carpet mixture having a nylon-6 content of 47.1 wt. %, the sieving yield being 18%. This primary rich carpet mixture is advantageously used as enriched carpet mixture, and subjected to depolymerisation conditions for nylon-6.

Example II

The overs fraction from the upper deck and the overs fraction from the lower deck of example I can be combined, and used as a primary rich carpet mixture having a nylon-6 content of 36 wt. %, the sieving yield being 89%. This primary rich carpet mixture is advantageously used as enriched carpet mixture, and subjected to depolymerisation conditions for nylon-6.

Example III

Carpets which had not been shredded into strips (average composition 28.5 wt. % nylon-6, 4.6 wt. % polypropylene, 36.6 wt. % $CaCO_3$ and 26.9 wt. % styrene butadiene rubber) were fed to the shredder at an average rate of 2500 kg/hour. The shredder was operated at 150 rpm. A loosened carpet mixture comprised of backing particles and nylon fibres was recovered from the shredder. The carpet mixture was distributed over the upper deck of screening apparatus. The upper deck was provided with 7 sieve plates with openings of 15×25 mm, followed by 7 sieve plates with openings of 28×35 mm, seen in the direction of transport of the open-end carpet mixture. The lower deck was provided with 4 sieve plates with openings of 2×8 mm, followed by 10 sieve plates with openings of 10×24 mm, seen in the direction of transport. Three streams of material were obtained which were continuously recovered. At some point in time 510 kg material with a nylon content of 41.3 wt. % had been as an overs fraction from the upper deck, 180 kg material with a nylon content of 34.3 wt. %, had been recovered as an overs fraction from the lower deck, and 810 kg material with a nylon content of 16.3 wt. % were recovered as an unders fraction from the lower deck.

The overs fraction from the upper deck can be used as a primary rich carpet mixture having a nylon-6 content of 41.3 wt. %, the sieving yield being 52%. This primary rich carpet mixture is advantageously used as enriched carpet mixture, and subjected to depolymerisation conditions for nylon-6.

Example IV

The overs fraction from the upper deck and the overs fraction from the lower deck of example III can be combined, and used as a primary rich carpet mixture having a nylon-6 content of 39 wt. %, the sieving yield being 67%. This primary rich carpet mixture is advantageously used as enriched carpet mixture, and subjected to depolymerisation conditions for nylon-6.

Figure 2:
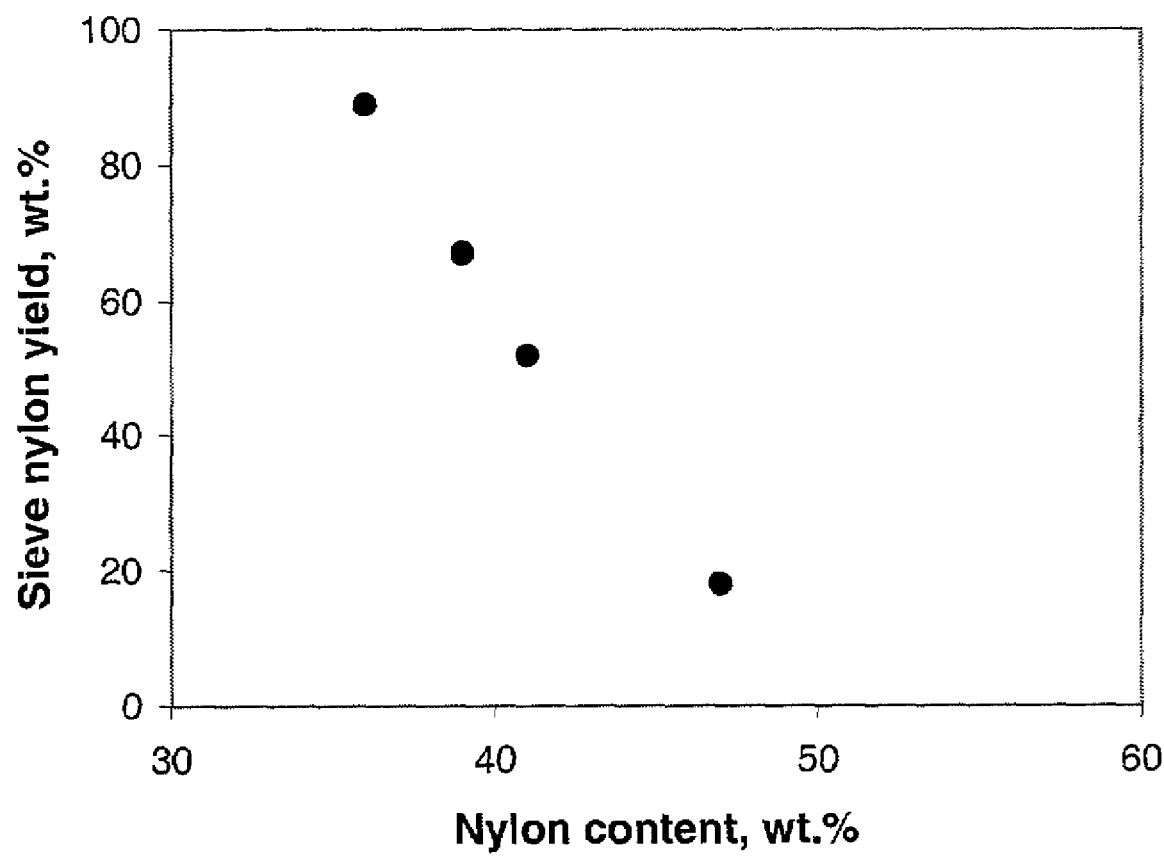
FIG. 2 shows the sieving yield as a function of the nylon content in primary rich carpet mixtures obtained in examples I to IV.
Figure 3:
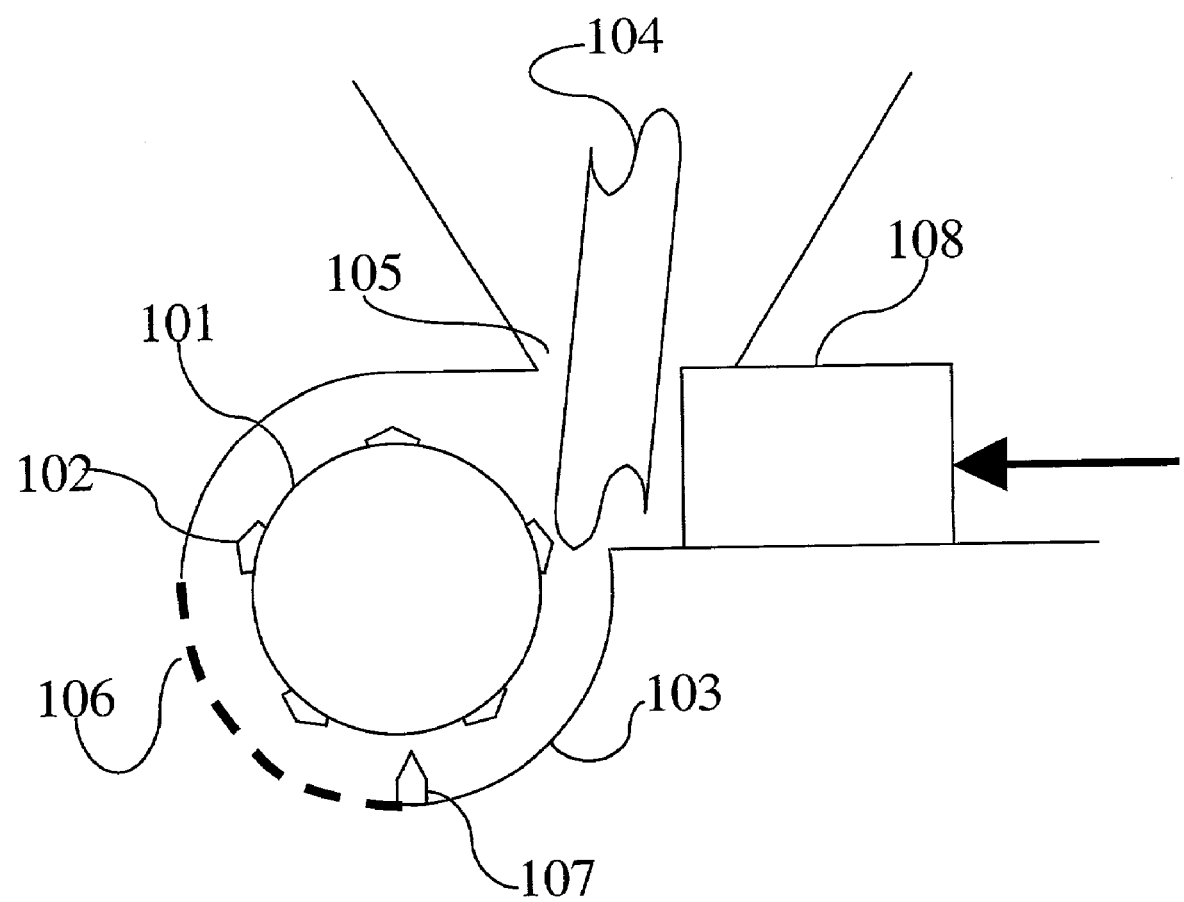
FIG. 3 shows a schematic side view of a preferred embodiment of a shredder.

FIG. 2 shows the sieving yield as a function of the nylon content for the primary rich carpet mixtures as obtained in examples I to IV. It can clearly be seen that the sieving yield decreases with increasing nylon content in the primary rich carpet mixture.

The invention claimed is:

1. Process for recovering monomeric units of a nylon from carpet material, said carpet material comprising fibres containing said nylon bound to a backing containing one or more non-nylon components, the carpet material containing between 15 and 35 wt. % of said nylon, which process comprises the steps of:
   a) mechanically separating the carpet material into an enriched carpet mixture containing between 35 and 55 wt. % of said nylon and into a depleted carpet mixture having a lower content of said nylon than the carpet material, by
      a1) mechanically treating the carpet material (1), using a shredder with knives, the knives being sufficiently blunt so as to size reduce the backing and to loosen at least 15 wt. % of the fibres from the backing, resulting in a primary loosened carpet mixture (2) comprising backing particles and fibres; and
      a2) sieving the primary loosened carpet mixture (2) to obtain said enriched carpet mixture (3) and said depleted carpet mixture (4), the enriched carpet mixture having in the range between 35 and 55 wt % nylon, which is a higher content of said nylon than the nylon content in the primary loosened carpet mixture, the depleted carpet mixture having a lower content of said nylon than the primary loosened carpet mixture, whereby the viscosity of the enriched carpet mixture is decreased at the conditions at which depolymerization is effected, whereby the sieving yield, which is the total mass of the desired nylon in the enriched carpet mixture divided by the total mass of nylon in the primary loosened carpet mixture prior to sieving is increased over the range of 35 and 55 wt % nylon in the enriched carpet mixture; and
   b) exposing the enriched carpet mixture to conditions at which depolymerisation of said nylon is effected.

2. Process for recovering a carpet mixture from carpet material, said carpet material comprising fibres containing nylon bound to a backing containing one or more non-nylon components, the carpet material containing one or more non-nylon components, the carpet material containing between 15 and 35 wt. % of said nylon, which process comprises the step of:
   a) mechanically separating the carpet material into an enriched carpet mixture containing between 35 and 55 wt. % of said nylon and into a depleted carpet mixture having a lower content of said nylon than the carpet material, by
      a1) mechanically treating the carpet material (1), using a shredder with knives, the knives being sufficiently blunt so as to size reduce the backing and to loosen at least 15 wt. % of the fibres from the backing, resulting in a primary loosened carpet mixture (2) comprising backing particles and fibres, and
      a2) sieving the primary loosened carpet mixture (2) to obtain the enriched carpet mixture (3) and the depleted carpet mixture (4), the enriched carpet mixture having in the range between 35 and 55 wt % nylon, which is a higher content of said nylon than the nylon content in the primary loosened carpet mixture, the depleted carpet mixture having a lower content of said nylon than the primary loosened carpet mixture, whereby the viscosity of the resulting enriched carpet mixture in the molten condition is decreased, whereby the sieving yield, which is the total mass of the desired nylon in the enriched carpet mixture divided by the total mass of nylon in the primary loosened carpet mixture prior to sieving is increased over the range of 35 and 55 wt % nylon in the enriched carpet mixture.

3. Process according to claim 1, wherein step a2 is carried out using an elastic, deformable screen.

4. Process according to claim 2, wherein step a) further comprises the step of:
   a3) mechanically separating the depleted carpet mixture into a secondary rich carpet mixture and a secondary poor carpet mixture, the secondary rich carpet mixture having a higher content of said nylon than the depleted carpet mixture, the secondary poor carpet mixture having a lower content of said nylon than the depleted carpet mixture.

5. Process according to claim 4, wherein step a3 comprises the steps of:
   i) mechanically treating the depleted carpet mixture (4) so as to loosen fibres in the depleted carpet mixture from backing particles in the depleted carpet mixture, resulting in a secondary loosened carpet mixture (5);
   ii) sieving the secondary loosened carpet mixture (5) to obtain a secondary rich carpet mixture (7) and a secondary poor carpet mixture (6), the secondary rich carpet mixture having a higher content of said nylon than the secondary loosened carpet mixture, the secondary poor carpet mixture having a lower content of said nylon than the secondary loosened carpet mixture.

6. Process according to claim 5, wherein the secondary rich carpet mixture contains between 35 and 55 wt. % of said nylon.

7. Process according to claim 5, wherein after step i) and prior to step ii) the secondary loosened carpet mixture is subjected to an air classification step in which backing particles are separated from the secondary loosened carpet mixture.

8. Process according to claim 7, wherein the backing particles which are separated in the air classification step include styrene butadiene rubber particles.

9. Process according to claim 1, wherein said nylon is nylon-6.

10. Process according to claim 9, wherein step b) comprises:
   b1) contacting the enriched carpet mixture with superheated steam at a temperature of about 250° C. to about 400° C. and at a pressure within the range of about 1 atm. to about 100 atm. and substantially less than the saturated vapor pressure of water at said temperature wherein a caprolactam-containing vapor stream is formed.

11. Process for recovering a carpet mixture from carpet material, said carpet material comprising fibres containing nylon bound to a backing containing one or more non-nylon components, the carpet material containing one or more non-nylon components, the carpet material containing between 15 and 35 wt. % of said nylon, which process comprises:
   a) mechanically separating the carpet material into an enriched carpet mixture containing between 35 and 55 wt. % of said nylon and into a depleted carpet mixture having a lower content of said nylon than the carpet material, by
   a1) mechanically treating the carpet material (1), using a shredder with knives, the knives being sufficiently blunt so as to size reduce the backing and to loosen at least 15 wt. % of the fibres from the backing, resulting in a primary loosened carpet mixture (2) comprising backing particles and fibres
   a2) sieving the primary loosened carpet mixture (2) to obtain said enriched carpet mixture (3) and said depleted carpet mixture (4), the enriched carpet mixture having in the range between 35 and 55 wt % nylon, which is a higher content of said nylon than the nylon content in the primary loosened carpet mixture, the depleted carpet mixture having a lower content of said nylon than the primary loosened carpet mixture.

12. Process according to claim 11, further comprising recovering monomeric units of said nylon from said carpet material, comprising exposing the enriched carpet mixture to conditions at which depolymerisation of said nylon is effected.

13. Process according to claim 11, wherein the knives of the shredder are sufficiently blunt to loosen at least 15 wt. % of the fibres from the backing.

14. Process according to claim 11, wherein step a2 is carried out using an elastic, deformable screen.

15. Process according to claim 11, wherein step a) further comprises:
   a3) mechanically separating the depeleted carpet mixture into a secondary rich carpet mixture and a secondary poor carpet mixture, the secondary rich carpet mixture having a higher content of said nylon than the depleted carpet mixture, the secondary poor carpet mixture having a lower content of said nylon than the depleted carpet mixture.

16. Process according to claim 15, wherein step a3 comprises:
   i. mechanically treating the depleted carpet mixture (4) so as to loosen fibres in the depleted carpet mixture from backing particles in the depleted carpet mixture, resulting in a secondary loosened carpet mixture (5),
   ii. sieving the secondary loosened carpet mixture (5) to obtain a secondary rich carpet mixture (7) and a secondary poor carpet mixture (6), the secondary rich carpet mixture having a higher content of said nylon than the secondary loosened carpet mixture, the secondary poor carpet mixture having a lower content of said nylon than the secondary loosened carpet mixture.

17. Process according to claim 16, wherein the secondary rich carpet mixture contains between 35 and 55 wt. % of said nylon.

18. Process according to claim 16, wherein after step i) and prior to step ii) the secondary loosened carpet mixture is subjected to an air classification step in which backing particles are separated from the secondary loosened carpet mixture.

19. Process according to claim 18, wherein the backing particles which are separated in the air classification step comprise styrene butadiene rubber particles.

20. Process according to claim 11, wherein said nylon is nylon-6.

21. Process according to claim 12, wherein said nylon is nylon-6 and wherein step b) comprises:
   i) contacting the enriched carpet mixture with superheated steam at a temperature of about 250° C. to about 400° C. and at a pressure within the range of about 1 atm to about 100 atm and substantially less than the saturated vapor pressure of water at said temperature wherein a caprolactam-containing vapor stream is formed.

22. Process for obtaining a carpet mixture comprising fibres and backing particles from whole carpet and/or strips of whole carpet, said whole carpet comprising said fibres bound to a backing, which process comprises feeding the whole carpet and/or strips of whole carpet to a shredder, said shredder being provided with knives which are sufficiently blunt to effect size reduction of the backing and loosening of at least 15 wt. % of the fibres from the backing.

23. Process according to claim 11, wherein at least 20 wt % of the fibers are loosened from the backing in step a1).

* * * * *